(12) United States Patent
Sumi et al.

(10) Patent No.: US 11,826,161 B2
(45) Date of Patent: Nov. 28, 2023

(54) COGNITIVE FUNCTION EVALUATION DEVICE, COGNITIVE FUNCTION EVALUATION SYSTEM, COGNITIVE FUNCTION EVALUATION METHOD, AND NON-TRANSITORY COMPUTER-READABLE STORAGE MEDIUM

(71) Applicant: Panasonic Intellectual Property Management Co., Ltd., Osaka (JP)

(72) Inventors: Sadayuki Sumi, Hyogo (JP); Ryosuke Nagumo, Osaka (JP); Kengo Abe, Nara (JP); Yoshihiro Matsumura, Osaka (JP); Takashi Nishiyama, Hyogo (JP); Hirobumi Nakajima, Kyoto (JP); Kohji Sasabe, Osaka (JP); Makoto Kariyasu, Kyoto (JP); Takako Yoshimura, Hyogo (JP); Minoru Toyama, Oita (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 336 days.

(21) Appl. No.: 16/759,792

(22) PCT Filed: Oct. 15, 2018

(86) PCT No.: PCT/JP2018/038333
§ 371 (c)(1),
(2) Date: Apr. 28, 2020

(87) PCT Pub. No.: WO2019/087757
PCT Pub. Date: May 9, 2019

(65) Prior Publication Data
US 2020/0261014 A1    Aug. 20, 2020

(30) Foreign Application Priority Data

Nov. 2, 2017 (JP) .................................. 2017-213158

(51) Int. Cl.
*A61B 5/00* (2006.01)
*A61B 5/11* (2006.01)

(52) U.S. Cl.
CPC ............ *A61B 5/4088* (2013.01); *A61B 5/112* (2013.01); *A61B 5/742* (2013.01); *A61B 5/749* (2013.01); *A61B 2503/08* (2013.01)

(58) Field of Classification Search
None
See application file for complete search history.

(56) References Cited

U.S. PATENT DOCUMENTS 9,782,122 B1 * 10/2017 Pulliam ................ A61B 5/4839
2007/0162283 A1 * 7/2007 Petrushin ................ G10L 17/26
704/255

(Continued)

FOREIGN PATENT DOCUMENTS

JP    2004-240394 A    8/2004
JP    2011255106 A    12/2011

(Continued)

OTHER PUBLICATIONS

Noble, Kimberly, Guila Glosser, and Murray Grossman. "Oral reading in dementia." Brain and language 74.1 (2000): 48-69. (Year: 2000).*

(Continued)

*Primary Examiner* — Benjamin S Melhus
(74) *Attorney, Agent, or Firm* — Renner, Otto, Boisselle & Sklar, LLP

(57) ABSTRACT

A cognitive function evaluation device includes: an instruction unit that instructs quick pronunciation of pseudoword in which a predetermined syllable is repeated; an obtainment unit that obtains voice data indicating a voice of an evaluatee who has received an instruction; a calculation unit that calculates a feature from the voice data obtained by the (Continued)

obtainment unit; an evaluation unit that evaluates a cognitive function of the evaluatee from the feature calculated by the calculation unit; and an output unit that outputs a result of the evaluation by the evaluation unit.

6 Claims, 8 Drawing Sheets

(56) References Cited

U.S. PATENT DOCUMENTS

| | | | | |
|---|---|---|---|---|
| 2012/0053929 | A1* | 3/2012 | Hsia | G16H 50/30 704/9 |
| 2014/0073993 | A1* | 3/2014 | Poellabauer | A61B 7/00 600/586 |
| 2014/0107494 | A1 | 4/2014 | Kato | |
| 2015/0112232 | A1* | 4/2015 | Quatieri | A61B 5/7264 600/595 |
| 2015/0313497 | A1* | 11/2015 | Chang | A61B 5/377 600/544 |
| 2018/0286430 | A1* | 10/2018 | Shapira | A61B 5/7282 |
| 2019/0110754 | A1* | 4/2019 | Rao | G06N 7/00 |
| 2020/0365275 | A1* | 11/2020 | Barnett | A61B 5/4088 |

FOREIGN PATENT DOCUMENTS

| | | |
|---|---|---|
| JP | 2017-148431 A | 8/2017 |
| WO | 2012/165602 A1 | 12/2012 |

OTHER PUBLICATIONS

Glosser, Guila, et al. "Cognitive mechanisms for processing nonwords: Evidence from Alzheimer's disease." Brain and language 63.1 (1998): 32-49. (Year: 1998).*

Glosser, Guila, et al. "Repetition of single words and nonwords in Alzheimer's disease." Cortex 33.4 (1997): 653-666. (Year: 1997).*

Yu, Bea, et al. "Prediction of cognitive performance in an animal fluency task based on rate and articulatory markers." Fifteenth Annual Conference of the International Speech Communication Association. 2014. (Year: 2014).*

Williams, D., Payne, H. & Marshall, C. Non-word Repetition Impairment in Autism and Specific Language Impairment: Evidence for Distinct Underlying Cognitive Causes. J Autism Dev Disord 43, 404-417 (2013). https://doi.org/10.1007/s10803-012-1579-8 (Year: 2013).*

Mahmoudi, Zeinab, et al. "Classification of voice disorder in children with cochlear implantation and hearing aid using multiple classifier fusion." Biomedical engineering online 10.1 (2011): 1-18. (Year: 2011).*

Lansford, Kaitlin L., and Julie M. Liss. "Vowel acoustics in dysarthria: Speech disorder diagnosis and classification." (2014). (Year: 2014).*

Sapir, Shimon, et al. "Formant centralization ratio: A proposal for a new acoustic measure of dysarthric speech." (2010). (Year: 2010).*

International Search Report (ISR) and Written Opinion dated Nov. 20, 2018 in International (PCT) Application No. PCT/JP2018/038333.

Strinzel, Michaela et al. "Acoustic and Perceptual Correlates of Vowel Articulation in Parkinson's Disease With and Without Mild Cognitive Impairment: A Pilot Study", Speech and Computer,19th International Conference, SPECOM 2017, Aug. 13, 2017 (Aug. 13, 2017) p. 54-56.

Office Action dated Jun. 21, 2022 corresponding to Chinese Patent Application No. 201880070447.2.

Translation of the Search Report accompanying the Office Action corresponding to Chinese Patent Application 201880070447.2.

Chen, Xiaojuan et al. "Language and Speech Therapy for Exceptional Children", Nanjing Normal University Press, Jan. 31, 2015, pp. 169-170 and its English Translation.

Decision of Rejection dated Jan. 10, 2023 corresponding to Chinese Patent Application No. 201880070447.2.

Translation of the Search Report accompanying the Decision of Rejection corresponding to Chinese Patent Application 201880070447.2.

Search report dated Jun. 9, 2023 for corresponding Chinese patent application No. 201880070447.2.

Strinzel, Michaela et al. "Acoustic and Perceptual Correlates of Vowel Articulation in Parkinson's Disease With and Without Mild Cognitive Impairment: A Pilot Study", Speech and Computer,19th International Conference, SPECOM 2017, Aug. 13, 2017 (Aug. 13, 2017) p. 54-56. 56-64. Copy previously submitted; the original page numbering was incorrectly referenced in the Chinese office action cited on Jun. 21, 2022.

* cited by examiner

FIG. 7

|  | NORMAL CONTROLS (NC) | MILD COGNITIVE IMPAIRMENT (MCI) | ALZHEIMER'S DISEASE (AD) |
|---|---|---|---|
| NUMBER OF SUBJECTS | 90 | 94 | 93 |
| AVERAGE MoCA SCORE | 27.4 | 22.1 | 16.2 |
| MoCA SCORE RANGE | 25.2–29.6 | 19.0–25.2 | 11.4–21.0 |

COGNITIVE FUNCTION EVALUATION DEVICE, COGNITIVE FUNCTION EVALUATION SYSTEM, COGNITIVE FUNCTION EVALUATION METHOD, AND NON-TRANSITORY COMPUTER-READABLE STORAGE MEDIUM

TECHNICAL FIELD

The present disclosure relates to a cognitive function evaluation device, a cognitive function evaluation system, a cognitive function evaluation method, and a non-transitory computer-readable storage medium capable of evaluating the cognitive function of an evaluatee.

BACKGROUND ART

Typical tests for evaluating cognitive functions include the Hasegawa dementia scale-revised (HDS-R), the minimental state examination (MMSE), and the clinical dementia rating (CDR) that cause evaluatees being suspected patients, whose cognitive functions are to be evaluated, to answer questions on test papers. These methods are used for evaluatees in medical institutions by doctors, clinical psychologists, or other practitioners trained to some extent.

Such an evaluation method using test papers requires a long test time, that is, a burden on evaluatees. Repeatedly taking the same test, evaluatees may remember the answers. To solve these problems, disclosed is a technique that a doctor or any other practitioner records the voice of an evaluatee answering questions in a test and analyzes the voice of the evaluatee (see, e.g., Patent Literature (PTL) 1).

CITATION LIST

Patent Literature

PTL 1: International Publication No. WO2012/165602

SUMMARY OF THE INVENTION

Technical Problem

There is a demand for more simple and accurate evaluation on the cognitive function of an evaluatee.

To meet the demand, it is an objective of the present disclosure to provide a cognitive function evaluation device, for example, capable of simply and accurately evaluating the cognitive function of an evaluatee.

Solutions to Problem

A cognitive function evaluation device according to an aspect of the present disclosure includes: an instruction unit configured to give an instruction for quick pronunciation of pseudoword in which a predetermined syllable is repeated; an obtainment unit configured to obtain voice data indicating a voice of an evaluatee who has received the instruction; a calculation unit configured to calculate a feature from the voice data obtained by the obtainment unit; an evaluation unit configured to evaluate a cognitive function of the evaluatee from the feature calculated by the calculation unit; and an output unit configured to output a result of the evaluation by the evaluation unit.

A cognitive function evaluation system according to an aspect of the present disclosure includes: the cognitive function evaluation device; a voice collection device that detects the voice of the evaluatee; and a display device that displays the result of the evaluation output from the output unit. The instruction unit causes the display device to display an image to instruct the quick pronunciation of the pseudoword in which the predetermined syllable is repeated.

A cognitive function evaluation method to an aspect of the present disclosure is executed by a computer. The cognitive function evaluation method includes: giving an instruction for quick pronunciation of pseudoword in which a predetermined syllable is repeated; obtaining voice data indicating a voice of an evaluatee who has received the instruction; calculating a feature from the voice data obtained in the obtaining; and evaluating a cognitive function of the evaluatee from the feature calculated in the calculating to output a result of the evaluating.

The present disclosure may be implemented as a non-transitory computer-readable storage medium storing a program causing the computer to execute the cognitive function evaluation method.

Advantageous Effect of Invention

A cognitive function evaluation device, for example, according to the present disclosure allows simple and accurate evaluation on the cognitive function of an evaluatee.

BRIEF DESCRIPTION OF DRAWINGS

FIG. 7 shows scores acquired by evaluatees in a MoCA test.

DESCRIPTION OF EXEMPLARY EMBODIMENT

Now, an embodiment will be described with reference to the drawings. Note that the embodiment described below is a mere comprehensive or specific example of the present disclosure. The numerical values, shapes, materials, constituent elements, the arrangement and connection of the constituent elements, steps, step orders etc. shown in the following embodiment are thus mere examples, and are not intended to limit the scope of the present disclosure. Among the constituent elements in the following embodiment, those not recited in any of the independent claims defining the broadest concept of the present disclosure are described as optional constituent elements.

The figures are schematic representations and not necessarily drawn strictly to scale. In the figures, substantially the same constituent elements are assigned with the same reference marks, and redundant descriptions will be omitted or simplified.

The following embodiment employs expressions for directions. For example, "horizontal" means not only "completely horizontal" but also "substantially horizontal", that is, including differences of about several percent, for example.

Embodiment

Configuration of Cognitive Function Evaluation Device

Figure 1:
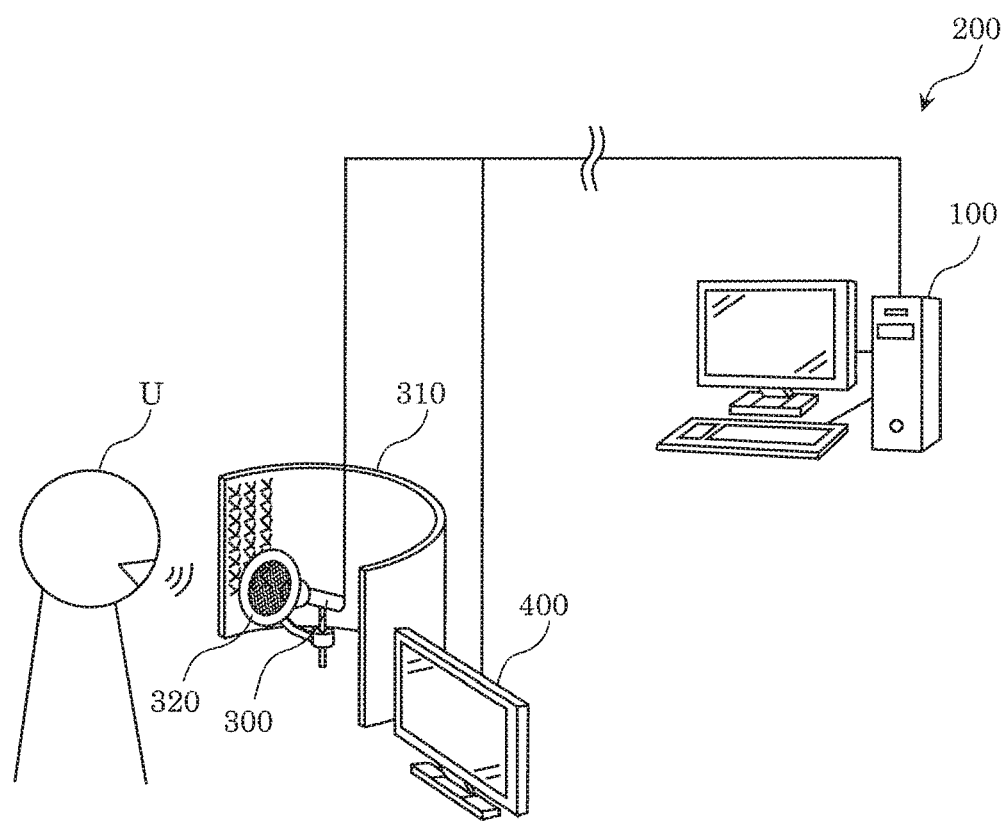
FIG. 1 shows a configuration of a cognitive function evaluation system according to an embodiment.

A configuration of a cognitive function evaluation system according to the embodiment will be described. FIG. 1 shows the configuration of the cognitive function evaluation system according to the embodiment.

Cognitive function evaluation system 200 is for evaluating the cognitive function of evaluatee U from the voice of evaluatee U. The cognitive function represents capabilities such as recognition, remembering, or judgment. As a specific example, cognitive function evaluation device 100 evaluates whether evaluatee U has dementia (i.e., whether the evaluatee is a dementia patient).

The symptoms of dementia include a decline in the cognitive function described above. Specific examples of dementia include Alzheimer's disease (AD). Since dementia patients are often not aware of any symptoms, the family of a suspected dementia patient or a third person encourages him/her to receive a medical examination at a hospital. Only then, the suspected patient sees a doctor. Alternatively, evaluatee U takes a batch test for dementia, such as the Montreal cognitive assessment (MoCA) test, to check whether evaluatee U has dementia.

The MoCA test takes, however, about 15 minutes each time. The MoCA test needs to be conducted a plurality of times at an interval to examine evaluatee U's change over time, thereby determining whether evaluatee U has dementia. That is, one set of the MoCA test requires a long time to examine whether evaluatee U has dementia.

It is known that there tends to be a difference in the voice between dementia patients and non-dementia people (i.e., healthy people), even when they utter the same word.

Cognitive function evaluation system 200 analyzes the voice of evaluatee U, thereby accurately evaluating the cognitive function of evaluatee U.

As shown in FIG. 1, cognitive function evaluation system 200 includes cognitive function evaluation device 100, voice collection device 300, and display device 400.

Cognitive function evaluation device 100 is a computer that evaluates the cognitive function of evaluatee U from voice data obtained by voice collection device 300 and indicating the voice of evaluatee U.

Voice collection device 300 is a microphone that detects the voice of evaluatee U and outputs voice data indicating the detected voice to cognitive function evaluation device 100. In order to accurately detect the voice of evaluatee U, isolation shield 310 and/or pop guard 320 may be arranged around voice collection device 300.

Display device 400 displays images based on image data output from cognitive function evaluation device 100. Specifically, display device 400 is a monitor device such as a liquid crystal panel or an organic EL panel. Display device 400 may be an information terminal such as a television, a smartphone, or a tablet terminal.

Cognitive function evaluation device 100, voice collection device 300, and display device 400 may be connected in a wired or wireless fashion, as long as capable of sending and receiving voice data or image data.

Cognitive function evaluation device 100 analyzes the voice of evaluatee U based on the voice data detected by voice collection device 300, evaluates the cognitive function of evaluatee U from the result of the analyzation, outputs image data for allowing display of an image indicating the result of the evaluation to display device 400. This configuration causes cognitive function evaluation device 100 to notify a dementia patient, who is not aware of any symptoms, of the cognitive function level and thus to encourage the dementia patient, for example, to see a doctor. In other words, cognitive function evaluation device 100 notifies a dementia patient, who is not aware of any symptoms, of the cognitive function level, thereby encouraging the dementia patient to see a doctor.

Note that cognitive function evaluation device 100 is a personal computer, for example, but may be a server device.

Figure 2:
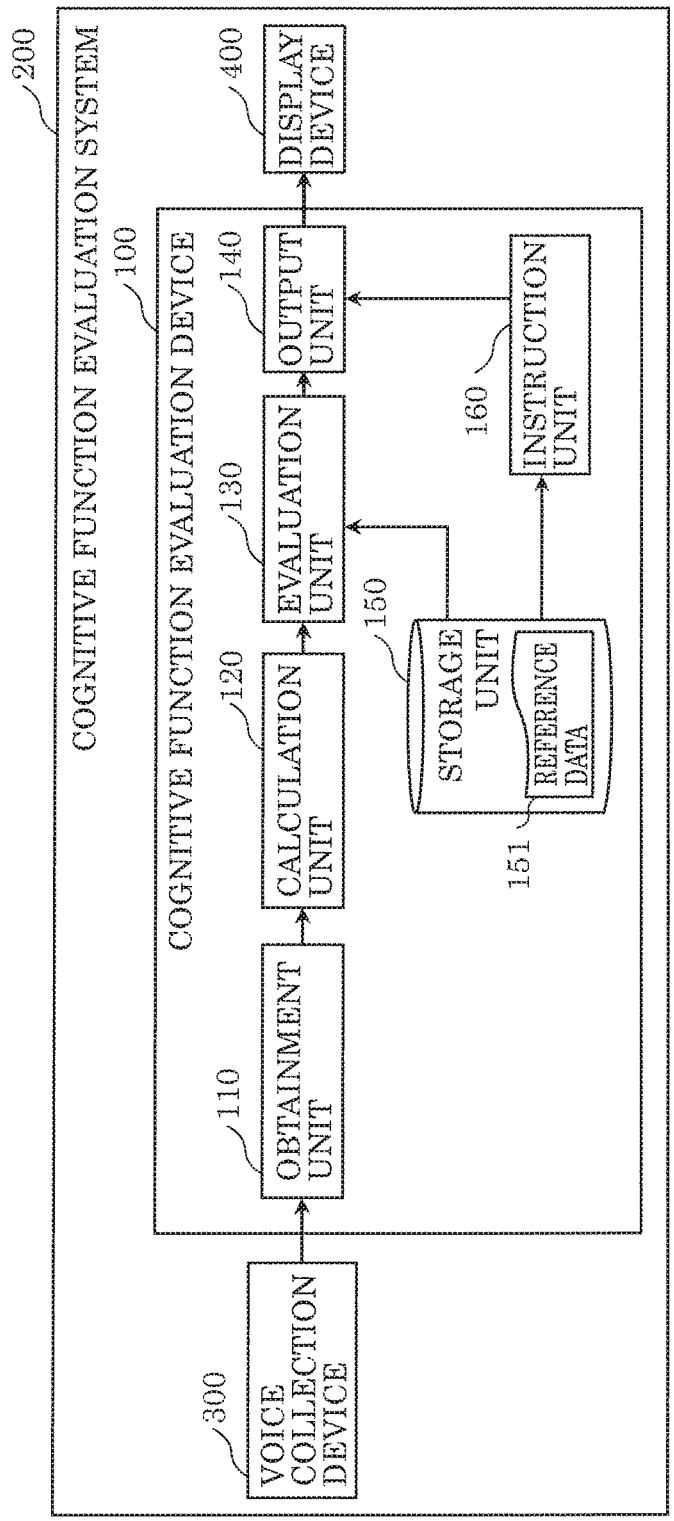
FIG. 2 is a block diagram showing a characteristic functional configuration of the cognitive function evaluation system according to the embodiment.

FIG. 2 is a block diagram showing a characteristic functional configuration of cognitive function evaluation device 100 according to the embodiment. Cognitive function evaluation device 100 includes obtainment unit 110, calculation unit 120, evaluation unit 130, output unit 140, storage unit 150, and instruction unit 160.

Obtainment unit 110 obtains the voice data detected by voice collection device 300. For example, obtainment unit 110 is a communication interface that performs wired or wireless communications, for example.

Calculation unit 120 is a processing unit that analyzes the voice data on evaluatee U obtained by obtainment unit 110. Specifically, calculation unit 120 may be a processor, a microcomputer, or a dedicated circuit.

Calculation unit 120 calculates a feature from the voice data obtained by obtainment unit 110. The feature is here a numerical value calculated from the voice data to be used by evaluation unit 130 for evaluating the cognitive function of evaluatee U and indicating the feature of the voice of evaluatee U. For example, the feature is based on a formant obtained from a vowel in the voice data obtained by obtainment unit 110. More specifically, the feature is a variation in a first formant, a variation in a second formant, or a variation in the ratio between the first and second formants, for example. Note that a "formant" means the frequency of a formant in the following embodiment. The variations are expressed by standard deviations, for example. In terms of a formant, additional description will be made later.

Evaluation unit 130 compares the feature calculated by calculation unit 120 and reference data 151 stored in storage unit 150, and evaluates the cognitive function of evaluatee U. Specifically, evaluation unit 130 is a processor, a microcomputer, or a dedicated circuit.

Output unit 140 outputs the result of the evaluation on the cognitive function of evaluatee U by evaluation unit 130 to display device 400. Output unit 140 is a communication interface that performs wired or wireless communications, for example.

Storage unit 150 is a storage device that stores reference data 151 indicating the relationship between a feature and a cognitive function. Reference data 151 is referenced by evaluation unit 130 in evaluating the cognitive function level of evaluatee U. Storage unit 150 is a read-only memory (ROM), a random-access memory (RAM), a semiconductor memory, or a hard disk drive (HDD), for example.

Storage unit 150 also stores programs executed by calculation unit 120 and evaluation unit 130 and image data to be used in outputting the result of the evaluation on the cognitive function of evaluatee U and indicating the result of the evaluation. In addition, storage unit 150 stores images for instructions, which will be described later.

Instruction unit 160 instructs quick pronunciation of a pseudoword in which a predetermined syllable is repeated. Specifically, instruction unit 160 obtains image data on the images for instructions on the quick pronunciation of the pseudoword in which the predetermined syllable is repeated stored in storage unit 150. The instruction unit then outputs the image data through output unit 140 to display device 400. In this manner, instruction unit 160 causes display device 400 to display the images for instructions, thereby instructing the quick pronunciation of the pseudoword in which the predetermined syllable is repeated.

Specifically, instruction unit 160 is a processor, a microcomputer, or a dedicated circuit. Note that calculation unit 120, evaluation unit 130, and instruction unit 160 may be integrated in a single processor, a microcomputer, or a dedicated circuit with corresponding functions, or may be achieved by a combination of two or more of: processors; microcomputers; and dedicated circuits.

Processing Procedure of Cognitive Function Evaluation Method

Figure 3:
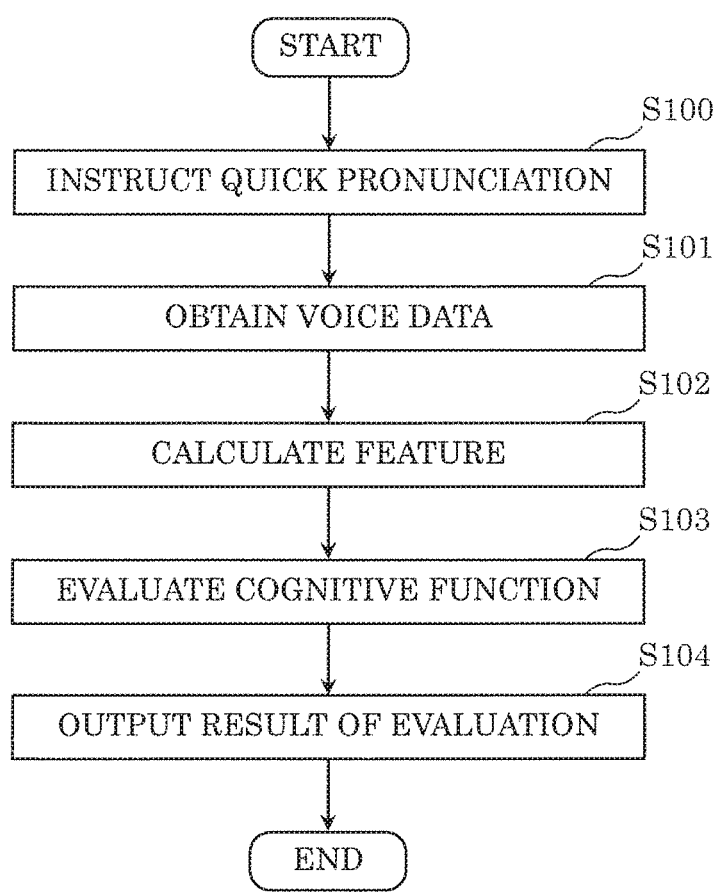
FIG. 3 is a flowchart showing a processing procedure of a cognitive function evaluation device according to the embodiment evaluating the cognitive function of an evaluatee.
Figure 4:
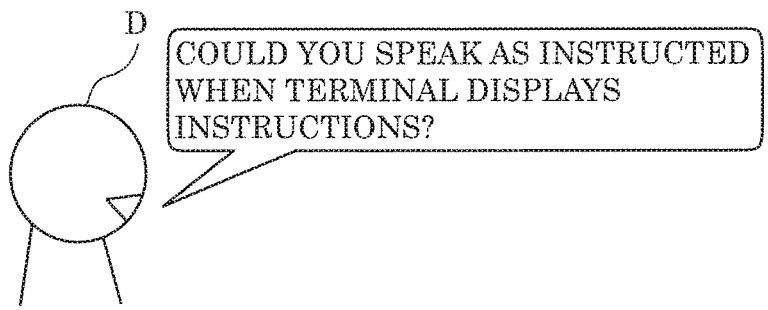
FIG. 4 shows an outline of a method of obtaining the voice of evaluatee U using the cognitive function evaluation device according to the embodiment.
Figure 4:
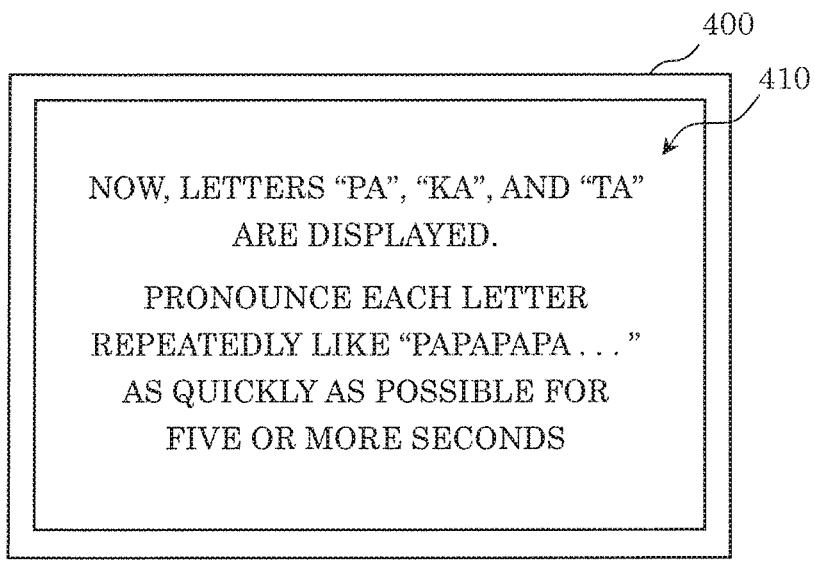
Figure 4:
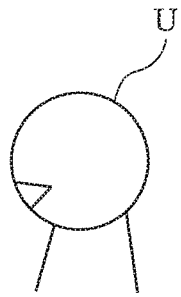

Now, a specific processing procedure of a cognitive function evaluation method executed by cognitive function evaluation device 100 will be described. FIG. 3 is a flowchart showing a processing procedure of cognitive function evaluation device 100 evaluating the cognitive function of an evaluatee. FIG. 4 shows an outline of a method of obtaining the voice of evaluatee U using cognitive function evaluation device 100.

First, instruction unit 160 instructs the quick pronunciation of the pseudoword in which the predetermined syllable is repeated (step S100). As shown in (a) of FIG. 4, for example, in step S100, doctor D or any other practitioner says to evaluatee U that "could you speak as instructed when an instruction is displayed on the terminal?". Instruction unit 160 obtains image data on images for instructions to evaluatee U stored in storage unit 150 and outputs the image data through output unit 140 to display device 400. As shown in (b) of FIG. 4, display device 400 then displays image 410 for instructions to evaluatee U. In this manner, image 410 for instructions to evaluatee U is displayed not to cause a noise in the voice data as compared to the case where doctor D instructs evaluatee U with his/her own voice.

Specifically, image 410 for instructions is for instructing evaluatee U to quickly and repeatedly pronounce the predetermined syllable. Such a configuration that causes evaluatee U to quickly pronounce a pseudoword with repetition of the predetermined syllable is suitable for calculating a variation in a formant.

The predetermined syllable consists of, for example, a stop consonant and a vowel subsequent to the stop consonant. This configuration of the predetermined syllable allows accurate evaluation on the cognitive function of evaluatee U. In the Japanese language, examples of such a predetermined syllable include "pa", "ta", and "ka". The stop consonant includes a plosive and an affricate, for example. The plosive and the affricate are the sounds made by completely closing both the oral and nasal tracts to increase the inside pressure and then releasing the pressure.

Image 410 for an instruction instructs pronunciation of the predetermined syllable for five seconds or more. That is, instruction unit 160 instructs the pronunciation of the pseudoword with repetition of the predetermined syllable for five seconds or more. As a result, obtainment unit 110 obtains the voice data that lasts five seconds or more. Accordingly, cognitive function evaluation device 100 obtains the voice data with a length enough to calculate the variation in the first formant.

Next, obtainment unit 110 obtains the voice data on evaluatee U who has received the instruction in step S100 via voice collection device 300 (step S101). As shown in (c) of FIG. 4, in step S101, for example, evaluatee U reads the pseudoword such as "papapapapa . . . "; "tatatatata . . . "; or "kakakakaka . . . " aloud toward voice collection device 300. Obtainment unit 110 obtains, as the voice data, the voice of evaluatee U reading these pseudoword aloud.

After that, calculation unit 120 calculates the feature from the voice data obtained by obtainment unit 110 (step S102). In step S102, for example, calculation unit 120 identifies vowels in the voice data and calculates the feature based on the formant obtained from the spectrum of the identified vowels. Specifically, calculation unit 120 calculates, as the feature, the variation in the first formant obtained from the spectrum of the identified vowels. For example, if the voice data contains n predetermined syllables, where n is a natural number; n first formants are obtained. Using all or some of the first formants, the variations in the first formants can be calculated.

Note that calculation unit 120 may calculate, as the feature, the variation in the second formant obtained from the spectrum of the identified vowel. Calculation unit 120 may calculate, as the feature, the variation in the ratio between the first and second formants obtained from the spectrum of the identified vowel.

Next, evaluation unit 130 evaluates the cognitive function of evaluatee U from the feature calculated by calculation unit 120 in step S102 (step S103). In step S103, evaluation unit 130 evaluates the cognitive function of evaluatee U from, for example, the variation in the first formant calculated by calculation unit 120 in step S102 and reference data 151 stored in storage unit 150.

After that, output unit 140 outputs the result of the evaluation on the cognitive function of evaluatee U by evaluation unit 130 (step S104). In step S104, output unit 140 obtains, for example, image data on an image corresponding to the result of the evaluation by evaluation unit 130 in step S103 from storage unit 150 and sends the obtained image data to display device 400.

Figure 5:
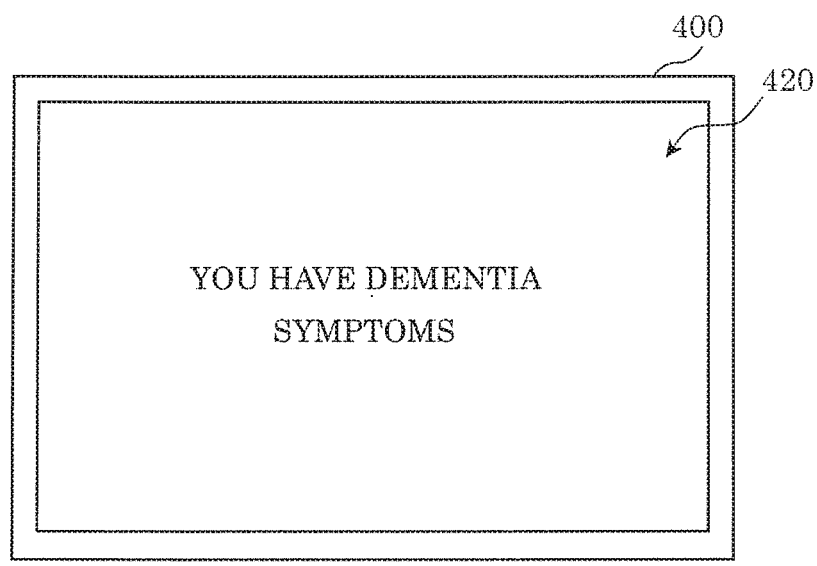
FIG. 5 shows an example image corresponding to a result of evaluation.

Display device 400 obtains the image data output from output unit 140 and displays the images based on the image data. FIG. 5 shows an example image corresponding to the result of the evaluation. The image shown in FIG. 5 indicates that evaluatee U has a lower cognitive function.

In this manner, the result of the evaluation is displayed as an image so that evaluatee U easily knows the result of the evaluation on the cognitive function. If evaluatee U evaluates the cognitive function using cognitive function evaluation device 100 at home or any other place, cognitive function evaluation device 100 may encourage evaluatee U to see a doctor or any other practitioner by displaying an image.

Formant

Figure 6:
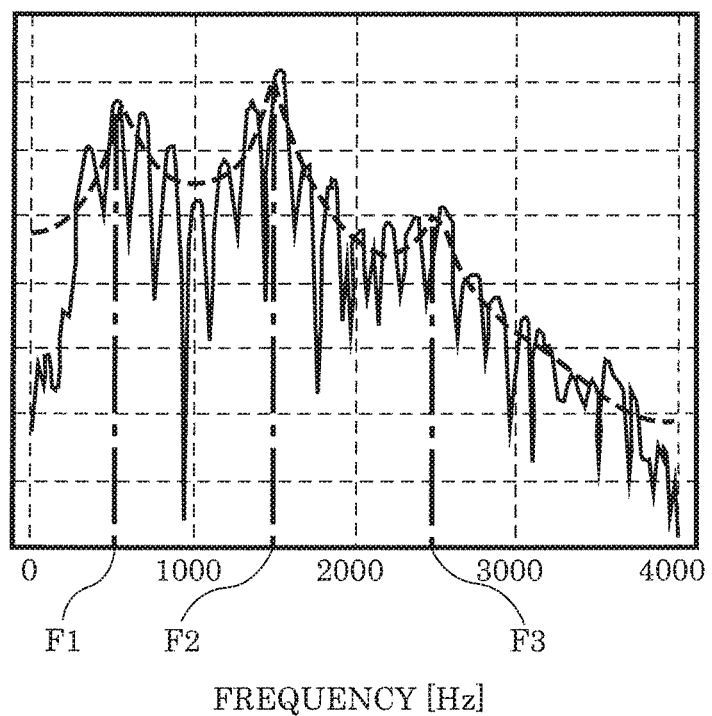
FIG. 6 illustrates a formant calculated from voice data by a calculation unit.

Now, the formant will be described additionally. FIG. 6 illustrates a formant calculated from the voice data by calculation unit 120. Specifically, FIG. 6 is a graph showing the spectrum obtained by converting the horizontal axis from the time to the frequency of the voice data. In FIG. 6, the vertical axis represents the amplitude.

As indicated by the broken lines in FIG. 6, a plurality of peaks are found in the data obtained by converting the horizontal axis of the voice data into the frequency. Out of the peaks, first formant F1 is the frequency with the lowest peak. Second formant F2 is the frequency with the second lowest peak next to first formant F1. Third formant F3 is the frequency with the third lowest peak next to second formant F2.

First formant F1 is a peak frequency that can be seen first, counting from the lowest frequency of the human voice. It is known that the first formant tends to reflect the feature related to the movement of the tongue. As compared to healthy people, dementia patients often fail to move their tongue well. It is thus considered that there tends to be a difference in first formant F1 between healthy people and dementia patients. Accordingly, the use of the amount related to the first formant as the feature leads to accurate evaluation on the cognitive function of evaluatee U.

Second formant F2 is a peak frequency that can be seen second, counting from the lowest frequency of the human voice. It is known that the second formant tends to reflect the influence related to the position of the tongue, out of the resonance caused by the vocal cord sound source in the vocal tract, the nasal cavity, and the oral cavity such as lips, and the tongue. As compared to healthy people, dementia patients often suffer from a decline in the motor function maintaining the position of the tongue or the chin. It is thus considered that there tends to be a difference in second formant F2 between healthy people and dementia patients. Accordingly, the use of the amount related to the second formant as the feature leads to accurate evaluation on the cognitive function of evaluatee U.

Calculation unit 120 extracts a vowel from the voice data, which have been obtained by obtainment unit 110, by a known method, and convers the voice data on the extracted vowel into data on the amplitude of the frequency to calculate the spectrum of the vowel, thereby calculating the formant. Note that the amplitude of the formant corresponds to the peak intensity at the frequency of the formant as shown in FIG. 6, for example.

According to the graph shown in FIG. 6, the calculation is made by converting the voice data into data on the amplitude of the frequency and then obtaining the envelope of the data. The envelope may be calculated by cepstral analysis or linear predictive coding (LPC), for example.

Specific Evaluation Method

In general, whether evaluatee U has dementia is examined by the MoCA test taken by evaluatee U. The MoCA test is a batch test for examination of dementia that allows determination on whether evaluatee U has dementia. FIG. 7 shows scores acquired by evaluatees U in the MoCA test.

The present inventors gathered evaluatees including healthy people with normal controls (NC), mild dementia patients with mild cognitive impairment (MCI), and dementia patients with AD to conduct the MoCA test. The number of evaluatees (i.e., the number of subjects) with NC was 90, the number of evaluatees with MCI was 94, and the number of evaluatees with AD was 93.

It is found from FIG. 7 that the average scores in the MoCA test (i.e., the average MoCA scores) and the score ranges in the MoCA test (i.e., the MoCA score ranges) are different among the NC, MCI, and AD groups. Specifically, the average score of the NC group in the MoCA was 27.4, the average score of the MCI group in the MoCA was 22.1, and the average score of the AD group in the MoCA was 16.2. Using, as reference data 151, the correlation between the results of the MoCA test obtained in this manner and variations in first formant F1, cognitive function evaluation device 100 evaluates the cognitive function of evaluatee U from the voice of evaluatee U and reference data 151.

Specifically, in reference data 151, there is a tendency that the larger the variation in the first formant is, the lower the cognitive function is. In view of this tendency, evaluation unit 130 evaluates, based on reference data 151, that the larger the variation in the first formant is, the lower the cognitive function is.

As described above, the feature may include, in addition to the variation in the first formant, the variation in the second formant or the variation in the ratio between the first and second formants. In these cases, evaluation unit 130 evaluates, for example, that the larger the variation in the second formant is, the lower cognitive function is; and that the larger the variation in the ratio between the first and second formants is, the lower cognitive function is.

The relationship between the variation and the cognitive function in the reference data described above is based on data analysis of the evaluatees gathered by the present inventors at present. In the future, data analysis may be performed with more evaluatees or under modified conditions, which may change the evaluation standard. Accordingly, it may be evaluated that the larger the variation in the first formant is, the higher the cognitive function is. It also applies to the variation in the second formant or the variation in the ratio between the first and second formants.

Other Examples of Feature

While calculating each feature based on the formant in the embodiment described above, calculation unit 120 may calculate any other feature.

For example, calculation unit 120 may calculate, as the feature, the fluctuation in the fundamental frequency of the voice data per unit time. The "fundamental frequency" means here the frequency of the sound source, that is, the interval of the voice of evaluatee U. The "fluctuation in the fundamental frequency . . . per unit time" means the amount of change in the fundamental frequency per unit time.

In this case, evaluation unit 130 evaluates, for example, that the larger the fluctuation in the fundamental frequency of the voice data per unit time is, the lower the cognitive function is. Instead, the evaluation unit may evaluate that the larger the fluctuation in the fundamental frequency of the voice data per unit time is, the higher the cognitive function is. Like reference data 151, the specific evaluation standard in this case may be determined experimentally or empirically as appropriate.

Calculation unit 120 may calculate, as the feature, the fluctuation amount of the fundamental frequency of the voice data per unit time. The fluctuation range of the fundamental frequency per unit time means the difference between the maximum and minimum values of the fundamental frequency per unit time.

In this case, evaluation unit 130 evaluates, for example, that the larger the fluctuation range of the fundamental frequency of the voice data per unit time is, the lower the cognitive function is. Instead, the evaluation unit may evaluate that the larger the fluctuation range of the fundamental frequency of the voice data per unit time is, the higher the cognitive function is. Like reference data 151, the specific evaluation standard in this case may be determined experimentally or empirically as appropriate.

Advantages

As described above, cognitive function evaluation device 100 includes instruction unit 160, obtainment unit 110, calculation unit 120, evaluation unit 130, and output unit 140. Instruction unit 160 gives an instruction for quick pronunciation of pseudoword in which a predetermined syllable is repeated. Obtainment unit 110 obtains voice data indicating the voice of evaluatee U who has received the instruction. Calculation unit 120 calculates the feature from the voice data obtained by obtainment unit 110. Evaluation unit 130 evaluates the cognitive function of evaluatee U from the feature calculated by calculation unit 120. Output unit 140 outputs the result of the evaluation by evaluation unit 130.

With this configuration, cognitive function evaluation device 100 obtains the voice data suitable for evaluating the cognitive function, thereby simply and accurately evaluating the cognitive function of evaluatee U.

For example, the predetermined syllable consists of a stop consonant and a vowel subsequent to the stop consonant.

Such a configuration of the predetermined syllable allows accurate evaluation on the cognitive function of evaluatee U.

For example, the predetermined syllable is any one of "pa", "ta", and "ka".

Such a configuration of the predetermined syllable allows accurate evaluation on the cognitive function of evaluatee U.

For example, obtainment unit 110 obtains voice data that lasts five seconds or more.

Accordingly, cognitive function evaluation device 100 obtains the voice data with a length sufficient to calculate the feature.

For example, calculation unit 120 identifies a vowel in the voice data and calculates the feature based on the formant obtained from the spectrum of the identified vowel.

Accordingly, cognitive function evaluation device 100 evaluates the cognitive function of evaluatee U from the feature based on the formant.

For example, calculation unit 120 calculates, as the feature, the variation in the first formant obtained from the spectrum of the identified vowel.

Accordingly, cognitive function evaluation device 100 evaluates the cognitive function of evaluatee U based on the variation in the first formant.

For example, calculation unit 120 calculates, as the feature, the variation in the second formant obtained from the spectrum of the identified vowel.

Accordingly, cognitive function evaluation device 100 evaluates the cognitive function of evaluatee U based on the variation in the second formant.

For example, calculation unit 120 calculates, as the feature, the variation in the ratio between the first and second formants obtained from the spectrum of the identified vowel.

Accordingly, cognitive function evaluation device 100 evaluates the cognitive function of evaluatee U based on the variation in the ratio between the first and second formants.

For example, calculation unit 120 calculates, as the feature, the fluctuation in the fundamental frequency of the voice data per unit time.

Accordingly, cognitive function evaluation device 100 evaluates the cognitive function of evaluatee U based on the fluctuation in the fundamental frequency of the voice data per unit time.

For example, calculation unit 120 calculates, as the feature, the fluctuation amount in the fundamental frequency of the voice data per unit time.

Accordingly, cognitive function evaluation device 100 evaluates the cognitive function of evaluatee U based on the fluctuation range of the fundamental frequency of the voice data per unit time.

Cognitive function evaluation system 200 according to the embodiment includes: cognitive function evaluation device 100, voice collection device 300, and display device 400. Voice collection device 300 detects the voice of the evaluatee and outputs voice data indicating the detected voice to obtainment unit 110. Display device 400 displays the result of the evaluation output from output unit 140. Instruction unit 160 causes display device 400 to display an image to instruct the quick pronunciation of the pseudoword in which the predetermined syllable is repeated.

With this configuration, cognitive function evaluation device 100 obtains voice data suitable for evaluating the cognitive function of evaluatee U, thereby simply and accurately evaluating the cognitive function.

The cognitive function evaluation method according to the embodiment is executed by a computer. The cognitive function evaluation method includes instructing quick pronunciation of pseudoword in which a predetermined syllable is repeated; obtaining voice data indicating a voice of evaluatee U who has received an instruction; calculating the feature from voice data obtained in the obtaining; evaluating a cognitive function of evaluatee U from the feature calculated in the calculating; and outputting a result of the evaluating.

With this procedure, cognitive function evaluation system 200 obtains the voice data suitable for evaluating the cognitive function of evaluatee U, thereby simply and accurately evaluating the cognitive function.

The present disclosure may be implemented as a program that causes a computer to execute the cognitive function evaluation method described above.

Such a program causes the computer to calculate the feature from voice data indicating the voice of evaluatee U, thereby simply and accurately evaluating the cognitive function of evaluatee U.

Variations

Now, cognitive function evaluation systems according to Variation 1 and Variation 2 of the embodiment will be described. Note that substantially the same constituent elements are assigned with the same reference marks, and redundant descriptions may be omitted or simplified.

Figure 8:
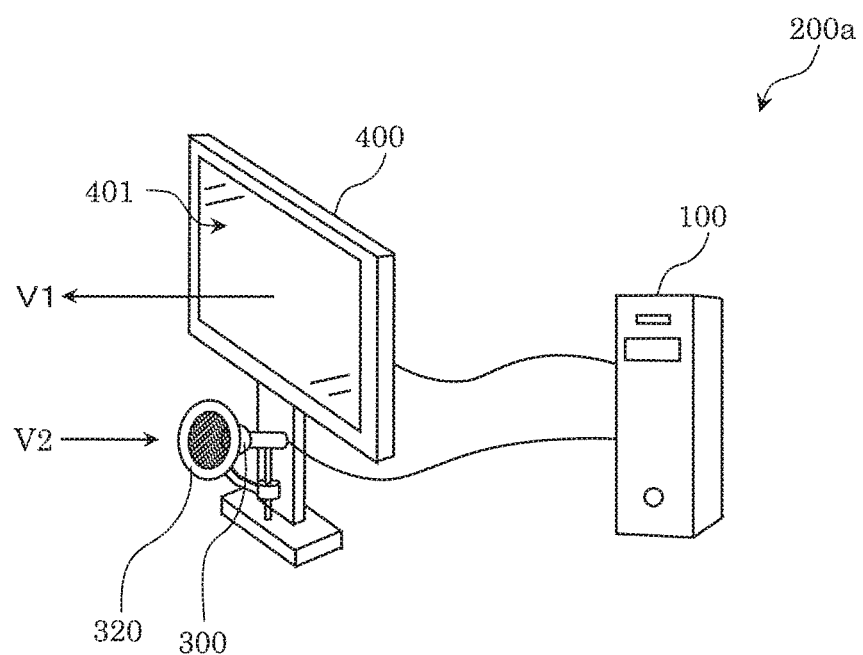
FIG. 8 shows a configuration of a cognitive function evaluation system according to Variation 1 of the embodiment.

FIG. 8 shows a configuration of the cognitive function evaluation system according to Variation 1 of the embodiment.

Like cognitive function evaluation system 200 according to the embodiment, cognitive function evaluation system 200a according to Variation 1 of the embodiment includes cognitive function evaluation device 100, voice collection device 300, and display device 400. Cognitive function evaluation system 200a may include pop guard 320 to cover voice collection device 300, for example.

Cognitive function evaluation system 200a employs directional voice collection device 300. Voice collection device 300 and display device 400 are here arranged such that the direction in which voice collection device 300 exhibits the maximum sensitivity (i.e., voice collection direction V2 shown in FIG. 8) agrees with normal direction V1 of display surface 401 on which display device 400 displays question information. Specifically, voice collection device 300 and display device 400 are arranged on a fixed object such as a desk such that normal direction V1 is parallel to voice collection direction V2. Note that voice collection device 300 and display device 400 may be fixed to a building material, for example. Cognitive function evaluation system 200a may include a fixture to establish a fixed positional relationship between voice collection device 300 and display device 400.

With this configuration, voice collection direction V2 tends to agree with the direction into which evaluatee U speaks even while viewing display device 400. The positional relationship as in cognitive function evaluation system 200a causes voice collection device 300 to accurately detect the voice of evaluatee U.

Now, the cognitive function evaluation system according to Variation 2 of the embodiment will be described.

Figure 9:
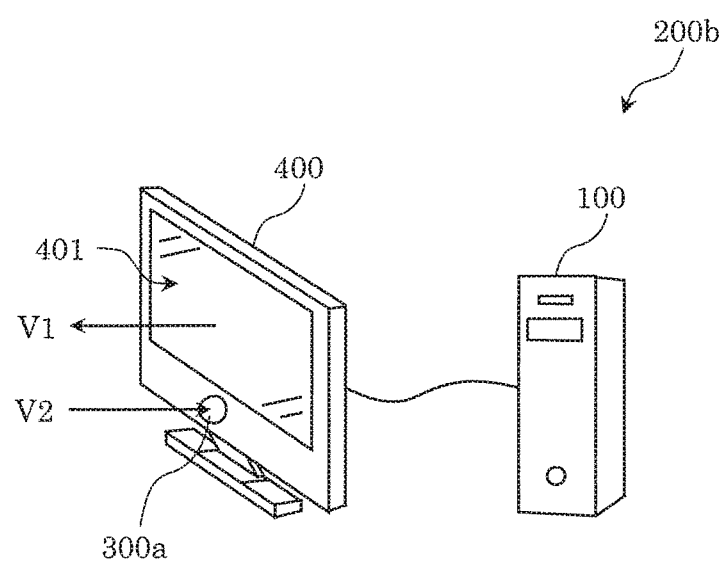
FIG. 9 shows a configuration of a cognitive function evaluation system according to Variation 2 of the embodiment.

FIG. 9 shows a configuration of the cognitive function evaluation system according to Variation 2 of the embodiment.

Like cognitive function evaluation system 200 according to the embodiment, cognitive function evaluation system 200b according to Variation 2 of the embodiment includes cognitive function evaluation device 100, voice collection device 300a, and display device 400.

Like voice collection device 300, voice collection device 300a is a microphone that detects the voice of evaluatee U and outputs voice data indicating the detected voice to cognitive function evaluation device 100. Like voice collection device 300 in cognitive function evaluation system 200a according to Variation 1 of the embodiment, voice collection device 300a is directional.

In cognitive function evaluation system 200b, voice collection device 300a and display device 400 are formed integrally. Specifically, voice collection device 300a and display device 400 are arranged in a housing. In the manufacturing process, voice collection device 300a and display device 400 may be integrally formed such that normal direction V1 agrees with voice collection direction V2. This may reduce the deviation between normal direction V1 and voice collection direction V2 when evaluatee U utilizes cognitive function evaluation system 200b.

Other Embodiments

The cognitive function evaluation systems or other elements have been described above in the embodiment and Variations 1 and 2 of the embodiment. The present disclosure is not limited to the embodiment and variations.

In the embodiment described above, the cognitive function evaluation device classifies the evaluatees into the ND, MCI, and AD groups as specific examples of evaluating the cognitive functions. The evaluation by the cognitive function evaluation device is however not limited to the classification into the ND, MCI, and AD groups. For example, the drunkenness of evaluatee U may be evaluated.

In the embodiment described above, Alzheimer's disease is named as a specific example of a decline in the cognitive function. The "cognitive function" represents, however, capabilities such as recognition, remembering, or judgment, and the symptoms of the "dementia" include a lower cognitive function as described above. That is, the cognitive function evaluation device evaluates the cognitive function levels not only in Alzheimer's disease but also in vascular dementia, for example.

In the embodiment described above, in order to evaluate the cognitive function level of evaluatee U, the data indicating the relationship between the scores in the MoCA test and the features based on the formants is stored, as reference data 151, in advance in storage unit 150. However, reference data 151 may be any data as long as being compared to the features of the formants to allow evaluation on the cognitive function level. The reference data is not limited to the data indicating the relationship between the scores in the MoCA test and the features of the formants. For example, the reference data may be data indicating the relationship between scores in a mini-mental state examination (MMSE), for example, and the features of formants.

The present disclosure may be implemented by a program that causes a computer to execute the steps executed by the cognitive function evaluation device. The present disclosure may also be implemented by a recording medium, such as a CD-ROM, readable by a computer recording the program. Alternatively, the present disclosure may be implemented by information, data, or signals indicating the program. The program, information, data, and signals may be delivered via a communication network such as internet.

In the embodiment described above, only the voice data obtained from the evaluatee is calculated as the feature to evaluates the cognitive function of the evaluatee. The evaluation may be performed however by combining data sets that allow evaluation on other known cognitive functions. For example, it is known that there is a correlation between a cognitive function and walking data, such as a step length, a step width, or a walking speed, related to walking. A combination of the voice data on the evaluatee evaluated in the embodiment described above and the walking data on the evaluatee may be used for the evaluation on the cognitive function, which leads to more accurate evaluation on the cognitive function of the evaluatee.

While the examples of the feature to be calculated by the calculation unit are raised in the embodiment described above, the evaluation unit may evaluate the cognitive function of the evaluatee from the plurality of different features calculated by the calculation unit. The evaluation unit may also evaluate the cognitive function of the evaluatee with the features weighted. The coefficients used by the evaluation unit for weighting may be determined freely.

The present disclosure includes other embodiments, such as those obtained by variously modifying the embodiment as conceived by those skilled in the art or those achieved by freely combining the constituent elements and functions in the embodiment without departing from the scope and spirit of the present disclosure.

The invention claimed is:

1. A cognitive function evaluation device, comprising:
   an instruction unit configured to instruct, by causing a display device to display an image, an evaluatee to, for a predetermined amount of time or longer, repeatedly pronounce each of pseudowords in each of which only a predetermined syllable is continuously repeated;
   an obtainment unit configured to connect to a microphone to obtain, for the predetermined amount of time or longer, voice data indicating a voice of the evaluatee who has received the instruction;
   a calculation unit configured to calculate a feature from the voice data obtained by the obtainment unit;
   an evaluation unit configured to evaluate a cognitive function of the evaluatee from the feature calculated by the calculation unit
   an output unit configured to obtain image data corresponding to a result of the evaluation by the evaluation unit and to send the obtained image data to be displayed by the display device, wherein
      a direction in which the microphone indicates a maximum sensitivity is parallel to a normal direction of a display surface of the display device,
      the calculation unit is configured to identify a vowel in the voice data and is configured to calculate the feature based on a formant obtained from a spectrum of the vowel identified; and
      the evaluation unit evaluates that the cognitive function of the evaluatee decreases as a variation in the formant increases.

2. The cognitive function evaluation device according to claim 1, wherein the predetermined syllable is any one of "pa", "ta", and "ka" each including a stop consonant and a vowel subsequent to the stop consonant, and the pseudowords include at least two of: a pseudoword in which "pa" is continuously repeated; a pseudoword in which "ta" is continuously repeated; and a pseudoword in which "ka" is continuously repeated.

3. The cognitive function evaluation device according to claim 1, wherein the predetermined amount of time corresponds to five seconds, and the obtainment unit obtains the voice data that lasts five seconds or more.

4. The cognitive function evaluation device according to claim 1, wherein the calculation unit is configured to calculate, as the feature, a variation in a first formant obtained from the spectrum of the vowel identified.

5. The cognitive function evaluation device according to claim 1, wherein the calculation unit is configured to calculate, as the feature, a variation in a second formant obtained from the spectrum of the vowel identified.

6. The cognitive function evaluation device according to claim 1, wherein the calculation unit is configured to calculate, as the feature, a variation in a ratio between a first formant and a second formant obtained from the spectrum of the vowel identified.

* * * * *